(12) United States Patent
Pickett et al.

(10) Patent No.: US 7,544,725 B2
(45) Date of Patent: Jun. 9, 2009

(54) LABELLED BEADS

(75) Inventors: Nigel Pickett, Manchester (GB);
Andrew James Sutherland, Kidderminster (GB)

(73) Assignee: Nanoco Technologies Limited, Manchester (GB)

(*) Notice: Subject to any disclaimer, the term of this patent is extended or adjusted under 35 U.S.C. 154(b) by 0 days.

(21) Appl. No.: 11/784,174

(22) Filed: Apr. 5, 2007

(65) Prior Publication Data
US 2007/0238126 A1 Oct. 11, 2007

(30) Foreign Application Priority Data
Apr. 5, 2006 (GB) .................... 0606845.6

(51) Int. Cl.
C08K 9/00 (2006.01)
C03C 25/26 (2006.01)
C12Q 1/68 (2006.01)

(52) U.S. Cl. .............. 523/200; 523/203; 523/205; 435/6

(58) Field of Classification Search .............. 523/200, 523/202, 205; 435/6
See application file for complete search history.

(56) References Cited

U.S. PATENT DOCUMENTS
4,609,689 A 9/1986 Schwartz et al.

FOREIGN PATENT DOCUMENTS
WO 02/04527 1/2002
WO 2005/021150 3/2005
WO 2006/017125 2/2006

OTHER PUBLICATIONS
Search Report issued by United Kingdom Patent Office on Sep. 14, 2006, for United Kingdom Patent Application No. GB0606845.6.

*Primary Examiner*—Jezia Riley
(74) *Attorney, Agent, or Firm*—Goodwin Procter LLP

(57) ABSTRACT

A labeled polymeric bead wherein individual beads comprise a primary particle formed of a synthetic polymeric material, and at least one secondary particle entrapped within the primary particle of the bead and being comprised of a synthetic polymer material incorporating reporter moieties.

16 Claims, 8 Drawing Sheets

Figure 1
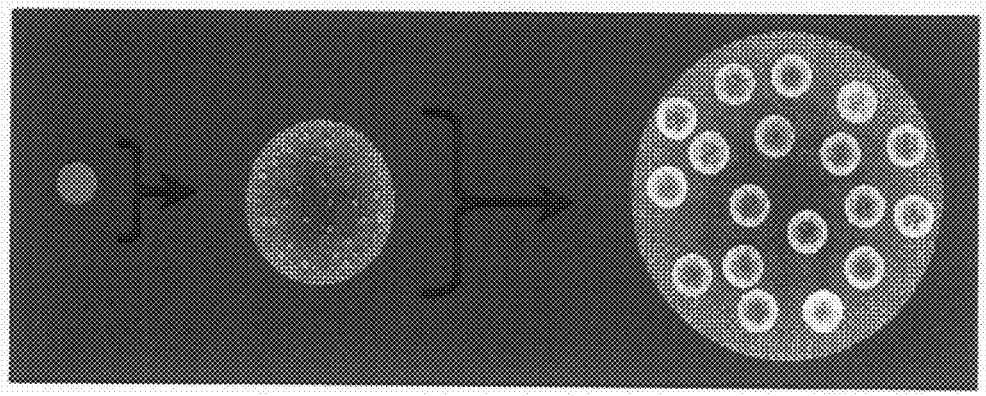
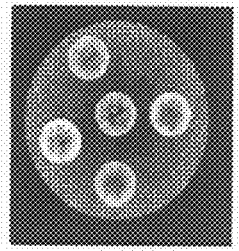 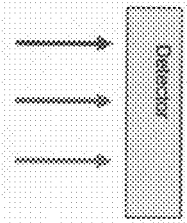  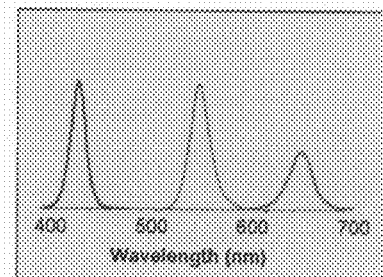
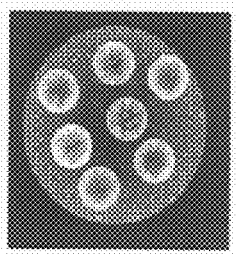 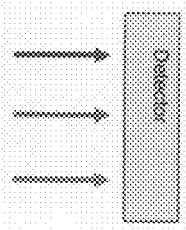  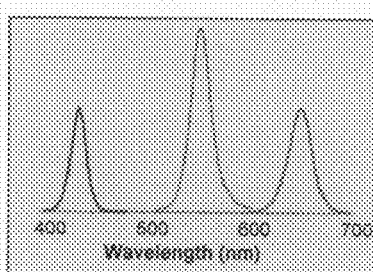
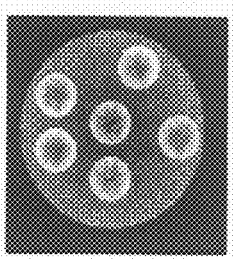 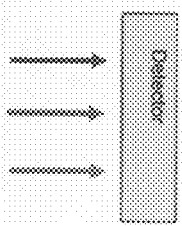  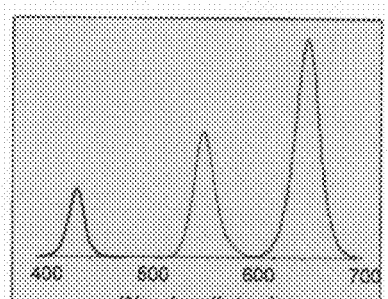

LABELLED BEADS

CROSS-REFERENCE TO RELATED APPLICATIONS

This application claims priority to and the benefit of United Kingdom Patent Application Serial No. 0606845.6, filed on Apr. 5, 2006, the disclosure of which is incorporated herein by reference in its entirety.

FIELD OF THE INVENTION

The present invention relates to particles labelled beads incorporating reporter moieties which are useful in a variety of applications for labelling and detection purposes. The term "beads" is used for convenience and is not intended to impose any particular shape limitation. Thus, for example, the beads may be spherical but other configurations are possible.

BACKGROUND OF THE INVENTION

Labelled beads have been used for many years in diagnostics testing, microscope-based assays, flow cytometry-based assays and combinatorial library synthesis. They also have potential to be used in a wide range of applications including biological monitoring, security/anti-counterfeiting, optical coding, biological assays, optical data storage and sensors.

A labelled bead will generally contain a plurality of reporter moieties. The reporter moieties may, for example, be fluorescent species such as fluorescent dyes or a quantum dot. (For the purposes of the present invention a single dye molecule or quantum dot is considered to be a reporter moiety). Further possibilities include the use of magnetic particles and specifically shaped particles as reporter moieties.

Labelled beads may contain different "species" of reporter moieties. Thus, for example, a labelled bead may contain two or more different types of fluorescent dye or two or more different types of quantum dot. Depending on the number of each species present, the bead will provide a particular signal which may in effect be considered to be a "bar-code". Put another way, there will be a first signal from the first species of reporter moiety, a second signal from the second species of reporter moiety etc. In addition the intensity of the signal from the first reporter moiety may be increased or decreased by the presence of the second reporter moiety. The particular combination of signals uniquely identifies the bead.

It will of course be appreciated that labelled beads may be produced with different combinations of reporter moieties so that different types of bead are distinguished by their "barcode" signal.

By way of illustration, such beads may be used for labelling ("tagging") proteins or nucleic acids. Thus molecules of a first type of nucleic acid or protein may be tagged (e.g. by incubation, covalent attachment, adsorption etc.) with labelled beads providing a first barcode signal. Similarly protein or nucleic acid molecules of a second type may be tagged with labelled beads providing a second barcode signal. The tagged protein or nucleic acids may then be admixed and subjected to a particular reaction. The individual barcodes allow the product mixture to be examined (e.g. after a separation procedure) to determine the origin of the tagged molecule in other words which specific reaction sequences the bead has been exposed to or else which known molecule has been attached to the bead).

Most of the bar-coded labelled particle libraries currently available have been produced by encoding beads with different concentrations of fluorescent dyes and/or metal (including magnetic metal) particles. In the case where the moieties are fluorescent dyes, the size of the library is limited by the overlapping excitation and emission spectra of the dyes. There are also limitations on libraries produced using metal particles as the reporter moieties.

Some of the above mentioned disadvantages are overcome by the use of quantum dots as the reporter moieties.

Quantum dots are a subset of nanoparticles that when excited emit light, with quantum yields of between 30-70% and narrow emission bands across the visible spectrum and extending to both the UV and near infrared spectrum. Compared with conventional fluorescent probes (e.g. organic dyes and lanthanides) quantum dots have a number of advantages. Most notably quantum dots absorb light over a wide range of wavelengths so a number of different light-emitting quantum dots can be stimulated using a single light source to produce an output in parallel, a so-called optical barcode. This is in contrast to conventional fluorescent compounds for which (i) their absorption and emission spectra are closely coupled (thus requiring a number of different light sources for multiplexing purposes), and (ii) their emission spectrum is often extremely broad and overlapping with its absorption spectra.

Labelled beads comprised of polymeric particles incorporating quantum dots have been proposed and may be produced, for example, by including the quantum dots in a suspension polymerisation procedure. One example of such a technique is disclosed in WO 2005/021150 (The University of Manchester) which leads to beads having a size of 0.5 microns upwards.

Typically one population of quantum dot is added to a single polymerisation reaction. All polymer particles produced in a batch from a polymerisation reaction will contain statistically approximately the same number of quantum dots with the average number of quantum dots per polymer particle being determined by the reagent ratios selected in the polymerisation procedure.

Since the number of Quantum Dots per particle is relatively similar it is not trivial to distinguish between two different polymer particles produced in the same polymerisation reaction. This is, in some respects, an advantage in that the product of one polymerisation reaction can be made to be detectably different from that of another polymerisation reaction so the two batches can be used as different labelled beads. However this approach means that one polymerisation reaction produces one batch of optically coded polymer particles. By extension, to generate for example ten differently encoded beads would require ten different polymerisation reactions. For utility in optically encoded systems a large number of encoded microbeads are required which in turn would require a large number of polymerisation reactions to be carried out.

In order to overcome this disadvantage, it is possible (but by no means trivial) to separate the beads obtained in one polymerisation reaction into a number of separate fractions such that the beads in one fraction effectively provide the same signal as each other but beads in different fractions provide signals which can be distinguished from each other by appropriately sensitive equipment. Therefore, in principle, this approach means that a single polymerisation reaction can yield two or more different fractions of labelled beads that can be distinguished from each other.

It is for example possible to sort the beads (incorporating quantum dots) obtained from one polymerisation reaction on the basis of the intensity of emission of each bead using a rapid sorting procedure such as a Fluorescence Activated Cell Sorter (FACS). Here the FACS instrument would be set to include, for example, emissions between two intensity levels and to exclude emissions above and below these levels—so-called "gating". One sorting procedure would then, for example, generate three different populations of beads. A quantity between a high and low cut-off level and two subsequent batches one above the higher cut off level and one below the lower cut-off level. However because the intensity cut-off point between one intensity level and the next is a continuum, sorting from one batch to another may result in some particles being placed in a different batch from one run to another i.e. the code fails.

This problem would be further exacerbated by the use of multiple machines where different machines will not possess exactly the same intensity calibration levels. A possible way round this problem would be to carry out a number of sorts based on intensities and simply discard particles that lie to close to a cut off point. However such an approach would be extremely time consuming (even with the phenomenal speed of FACS) and also result in the wastage of considerable amounts of materials (i.e. of encoded beads).

It is therefore an object of the present invention to obviate or mitigate the above mentioned disadvantages.

SUMMARY OF THE INVENTION

According to the present invention there is provided a labelled polymeric bead wherein individual beads comprise:

(a) a primary particle formed of a synthetic polymeric material, and (b) at least one secondary particle entrapped within the primary particle of the bead and being comprised of a synthetic polymer material incorporating reporter moieties, preferably at least around 500 reporter moieties.

Beads in accordance with the invention are capable of providing a detectable signal (generated by the reporter moieties on application of an appropriate stimulus) which is dependent on the total number of reporter moieties in the bead which in turn is dependent on the combination of:

(a) the number of secondary-particles in the primary particle; and (b) the number of types of secondary-particle in the primary particle.

As described more fully below, beads in accordance with the invention may easily be produced having different combinations of secondary-particles. Such beads (i.e. those having different combinations of secondary-particles) will contain significantly different total numbers of reporter moieties and are therefore readily distinguishable from each other.

Preferably the secondary particles include at least one reporter moiety and more preferably a plurality thereof. Generally there will be 1 to 1,000,000 secondary particles in each primary particle although more typically the number of secondary particles (per primary particle) will be 2 to 10,000, e.g. 2 to 5,000. For many embodiments of the invention there will be 5 to 100 secondary particles in each primary particle. Each secondary particle will generally contain at least around 500 reporter moieties to ensure that a detectable signal is provided by each secondary particle. Preferably each secondary particle contains at least around 750, more preferably at least 1000, and most preferably at least 10,000 reporter moieties. More preferably each secondary particle contains at least 100,000 (e.g. at least 1000000) reporter moieties. It can therefore easily be seen that beads containing (in the primary particle) different numbers of secondary will contain significantly different total numbers of reporter moieties so that such beads can be readily distinguished from each other.

Generally the primary particles will have a maximum cross-sectional dimension of 500 µm, e.g. 2 to 500 µm, e.g. 5 to 200 µm. Typically, the secondary particles will generally have a maximum cross-sectional dimension of 0.2 to 2 µm.

In a preferred embodiment of the invention, the reporter moieties (in the secondary particles) are quantum dots. The quantum dots may, for example, be core, core-shell or core-multi shell quantum dots. Other types of reporter moieties may for example be used, e.g. luminescent dyes, phosphors such as inorganic lanthanides, fluorescent compounds such as rhodamine, coloured/chromophoric compounds, other "up converting materials", Raman active compounds such as nitrile-containing compounds, NMR distinguishable isotopic labels such as $^{14}N/^{15}N$ nitrogen labelled compounds. With specific reference to fluorescent dyes and quantum dots, it is possible to use one tyre of dye or quantum dot which excites another type of dye or quantum dot by Fluorescence Resonance Energy Transfer (FRET). Reporter moieties can also include metallic particles/clusters (such as silver and gold particles), magnetic particles, radioisotopic labels or other compounds which possess a specific property/functionality that can be readily distinguished by a spectroscopic/analytic/non-destructive technique. An example of such a functional group containing reporter material would be an aldehyde or a nitrile both of which can be readily identified by infrared and Raman spectroscopy respectively. A further example would be a reporter material containing fluorine which can be identified by infrared and Raman spectroscopy.

The secondary particles (which are ultimately incorporated in the primary particles) may be formed by incorporating the reporter moieties in a polymerisation reaction which yields particles (e.g. having a diameter of 0.2 to 2.0 µm) incorporating the reporter moieties. Examples of polymerisation methods that may be used include suspension, dispersion, emulsion, living, anionic, cationic, RAFT, ATRP, bulk, ring closing metathesis and ring opening metathesis or else by any other method of incorporation into the polymer matrix of the larger polymeric particles. The polymerisation reaction will result in secondary particles containing statistically similar amounts of the reporter moieties.

The reporter moieties can be irreversibly incorporated in the secondary particles in a number of ways, e.g. chemical, covalent, ionic, physical (e.g. by entrapment) or any other form of interaction.

The secondary particles thus obtained can then be incorporated in a further polymerisation reaction to form primary particles incorporating a plurality of the secondary particles. Examples of polymerisation methods that may be used include suspension, dispersion, emulsion, living, anionic, cationic, RAFT, ATRP, bulk, ring closing metathesis and ring opening metathesis or else by any other method of incorporation into the polymer matrix of the larger polymeric particles.

The primary matrix of the secondary particles and/or the polymer matrix of the primary particles can be inert. Alternatively either or both matrices may be produced with a functionalised monomer. Alternatively either or both matrices may be functionalised after polymerisation.

The primary and secondary polymeric particles produced by these procedures may have any shape/morphology or 3-dimensional structure. Thus, for example, the particles may be spherical, disc-like, rod-like, ovoid, cubic or rectangular (many other configurations are also possible).

The polymerisation reaction for forming the primary particles may be effected using secondary particles of the same "type" (i.e. containing substantially the same numbers of the same reporter moieties), e.g. as obtained from a single polymerisation reaction for producing the secondary particles. For the purposes of the present invention, the term "same type" as applied to a sub-particle refers to sub-particles that contain approximately the same population of reporter moieties, i.e. within a narrowly defined distribution. Alternatively the polymerisation procedure for forming the primary particles may be effected using a mixture of different types of secondary particles, e.g. differing in numbers and/or nature of the reporter moieties.

The result of incorporating the secondary particles into the primary particles is that the resulting beads possess unique combinations of 'quanta' of one or more reporter material resulting in a distinct encoding pattern for that particular bead.

For example it is possible to mix separate batches of secondary particles containing (only) red quantum dots with batches containing further (separate) batches of secondary particles containing blue quantum dots and green quantum dots to give a population of secondary particles in the ratio of 10 blue:5 red:1 green.

These will then be incorporated into primary particles by any suitable polymerisation reaction to generate beads (containing the secondary particles) which possess distinct readable codes/signatures for example based on the colour and intensity of the three colours/channels of QD emissions (i.e. the number/'quanta' of smaller beads of each colour within each bigger bead). Beads resulting from this procedure having differing contents of secondary particles (e.g. different numbers of any one type of secondary particle) are readily distinguished from each other because of the significantly different total number of reporter moieties present in the bead. As such, the beads from the polymerisation reaction can readily be sorted into different fractions with the beads of each fraction being essentially identical to each other in turns of their detection characteristic but readily detectably different from beads in other fractions.

Differently sized reporter material-containing secondary particles can also be used to encode the larger polymeric particles. For example some blue QD-containing secondary particles of 2 μm and some red QD-containing smaller beads of 10 μm may be incorporated into the same population of primary particles. The resulting beads may then be distinguished from one another on the basis of both the size and colour of the secondary particles they contain.

Differently shaped reporter material-containing secondary particles can also be used to encode the primary particles. For example some blue QD-containing spherical secondary particles and some red QD-containing cubic secondary particles may be incorporated into the same population of primary particles. The resulting beads may then be distinguished from one another on the basis of both the shape and colour of the secondary particles they contain.

In addition the incorporation of specifically shaped reporter material-containing secondary particles into primary particles may confer specific shape related properties e.g. a dipole moment or a diffraction property, upon the resulting bead.

The primary and/or secondary particles may be chemically inert or alternatively may be chemically reactive/functionalised. The chemical functionality may be introduced during the construction of the particle, for example by the incorporation of a chemically functionalised monomer, or alternatively chemical functionality may be introduced in a post particle construction treatment for example a chloromethylation reaction. Additionally chemical functionality may be introduced by a post particle construction polymeric graft or other similar process whereby chemically reactive polymer (s) are attached to the outer layers of the reporter material containing polymeric particles. It will be obvious to those skilled in the art that more than one such post construction derivatisation process may be carried out to introduce chemical functionality onto/into the reporter material containing polymeric particles.

Although the invention has been described with specific reference to beads comprising primary particles and secondary particles, it should be understood that other constructions are within the ambit of the invention. Thus, for example, beads in accordance with the invention may comprise primary, secondary and tertiary particles. More specifically, the tertiary particles may contain reporter moieties, the secondary particles may contain various combinations of the tertiary particles, and the primary particles contain various combinations of the secondary particles.

A further possibility is a bead comprising a primary particle incorporating one or more secondary particles (each, in turn, incorporating one or more reporter moieties) and at least one polymeric shell provided around the primary particle. Each polymeric shell may itself incorporate one or more secondary particles. Thus, for example, assume that the primary particle is spherical. In this case, there may be one or more concentric polymer outer shells provided around the primary particle, each such shell incorporating one or more secondary particles.

BRIEF DESCRIPTION OF THE DRAWINGS

The invention will be further described by way of example only with reference to the accompanying drawings in which:

FIG. 1 schematically illustrates the structure of labelled beads in accordance with the invention and spectra obtained using examples of such particles;

FIG. 5($b$) a cross-sectional fluorescence emission fingerprint of the bead of FIG. 5($a$) (fingerprint taken along the line shown in FIG. 5($a$));

DETAILED DESCRIPTION OF THE INVENTION

Figure 2:
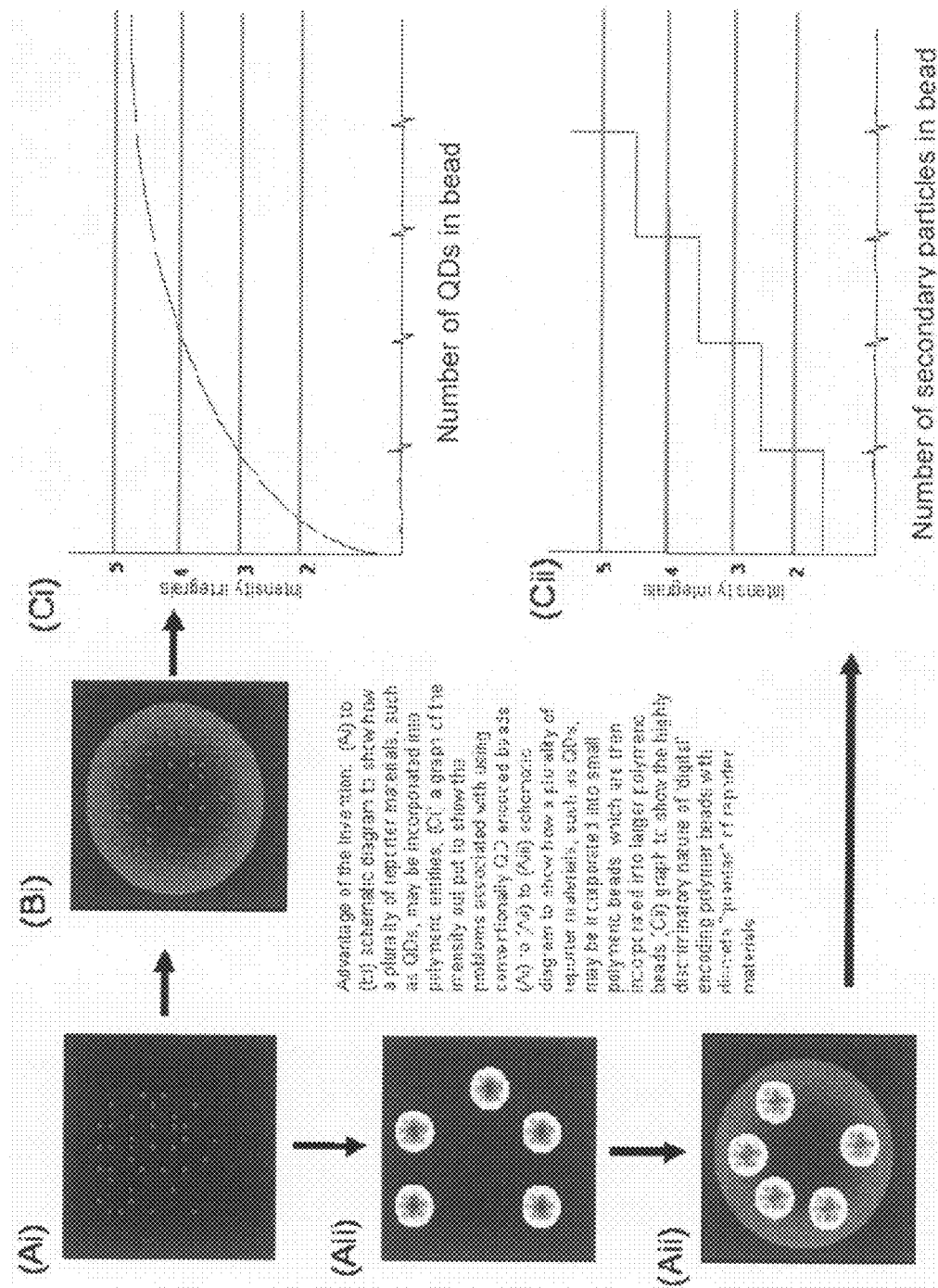
FIG. 2 schematically illustrates intensity outputs of (a) labelled beads in accordance with the invention, and (b) labelled beads of the prior art.

Reference is made firstly to FIG. 1(A) which, at the right hand side thereof, illustrates one embodiment of a labelled bead ("Suspension Polymerisation Particle") in accordance with the invention. This particle, which may for example have a size of 5-200 μm, is comprised of a polymeric matrix in which are embedded a plurality of secondary particles ("Dispersion Polymerisation Beads") each incorporating a population of quantum dots.

Each of these secondary particles may incorporate quantum dots of a single type but the type may vary between secondary particles. Thus for example some secondary particles (the "red secondaries") may incorporate a population of quantum dots that emit red light when excited by UV radiation, some (the "blue secondaries") may incorporate quantum dots that emit blue light and others (the "green secondaries") may incorporate quantum dots that emit green light.

Secondary particles that contain the same type of quantum dot will generally all contain approximately the same number thereof. However this number may be different for quantum dots of a different type. Thus, for example, the aforementioned "red secondaries" will each contain approximately the same number of quantum dots. However the "green secondaries" may contain a significantly different number of quantum dots (although the "green secondaries" will contain approximately the same number of quantum dots as each other). Similarly for the "blue secondaries".

It will be appreciated that, to produce the illustrated labelled particle, individual collections of red, green and blue sub-particles ("secondaries") are produced by dispersion polymerisation techniques using a reagent system incorporating quantum dots of the appropriate "colour".

Fractions of red, green and blue "secondaries" are then incorporated into a suspension polymerisation procedure to produce a collection of labelled particles of the type illustrated in FIG. 1A. This collection may then be readily sorted into fractions with the members of any one fraction containing exactly the same number of the different types of sub-particle.

FIG. 1(B) illustrates how labelled beads in accordance with the invention may readily be distinguished from each other in the case where individual beads have differing contents of secondary particles.

For the purposes of the following description, the beads depicted as (i)-(iii) in FIG. 1(B) are assumed to contain the following ratios of secondary particles of the indicated type (although in practice larger numbers of the various types of secondary particles are likely to be present).

| Bead No. | Red Secondary Particles | Blue Secondary Particles | Green Secondary Particles |
|---|---|---|---|
| (i) | 1 | 2 | 2 |
| (ii) | 2 | 2 | 3 |
| (iii) | 3 | 1 | 2 |

Again for the purposes of illustration, FIG. 1(B) shows the particles (i)-(iii) being illuminated with UV light which on emission from the particle is analysed by a detector to provide the emission spectra illustrated at the right hand side of FIG. 1(B), for which blue emission is represented by the left hand peak, green emission by the middle peak and red emission by the right hand peak.

It will be appreciated from FIG. 1(B) that particle (i) has a particular emission spectrum as governed by the number of red, blue and green secondary particles present in the bead. The spectrum of particle (i) is different from that of particles (ii) and (iii) which in turn are different from each other.

Thus the individual particles (i)-(iii) are readily distinguishable from each other.

FIG. 2 schematically illustrates how a collection of beads in accordance with the invention in which some of the beads contain a different number of secondary particles (incorporating quantum dots as reporter moieties) than others are much more readily distinguished from each other than are labelled beads of the prior art which comprise a single particle incorporating differing numbers of reporter moieties.

More specifically, the upper graph of FIG. 2 relates to the prior art labelled beads and the lower graph relates to labelled beads of the invention. The prior art labelled beads have been produced by a suspension polymerisation reaction conducted with quantum dots which has resulted in a collection of labelled beads containing a range of individual quantum dots. The "x-axis" of the upper graph in FIG. 2 represents (going from left to right) increasing numbers of quantum dots in the individual polymer particles of the prior art beads. The "y-axis" represents intensity of emission (arbitrary units). It will be seen from the upper graph of FIG. 2 that (for the prior art particles) a plot of number of quantum dots in the (prior art) beads vs intensity is a smooth curve.

Consider now, in contrast, the lower graph of FIG. 2 which relates to labelled beads of the invention. The "x-axis" of this graph represents the number of secondary particles in the beads and the "y-axis" again represents intensity (in arbitrary units). It can be seen that, for the labelled beads of the invention, a plot of number of secondary particles vs intensity is stepped such that each additional secondary particle produces a distinct rise in the intensity of the beads.

Figure 3:
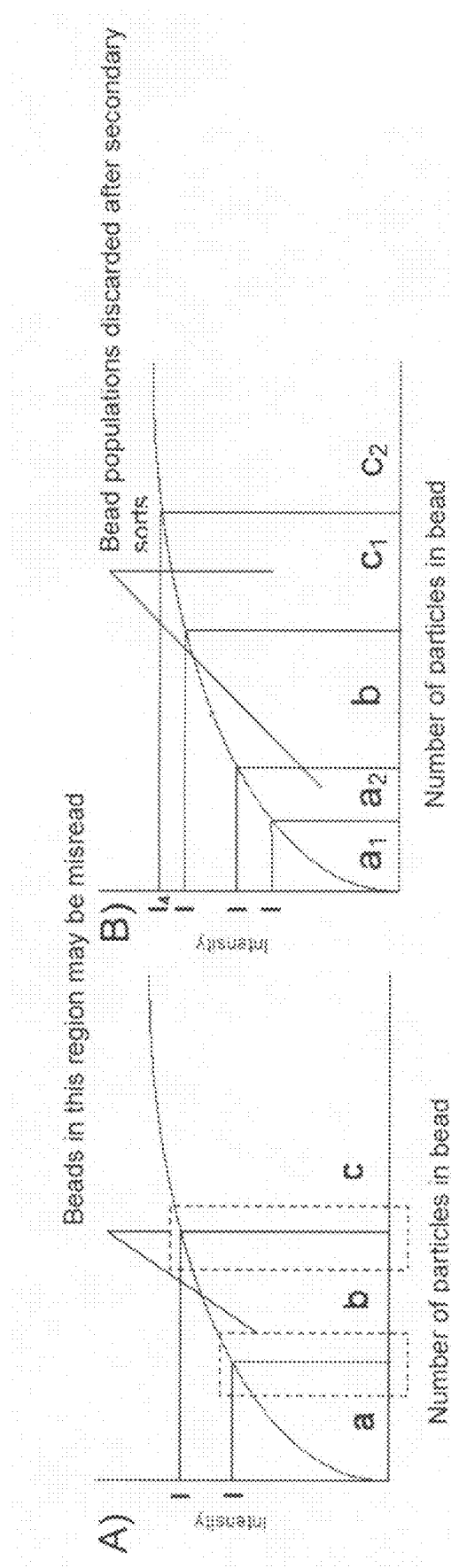
FIG. 3 schematically illustrates intensity-based sorts of (a) labelled beads in accordance with the invention, and (b) labelled beads of the prior art.
Figure 4:
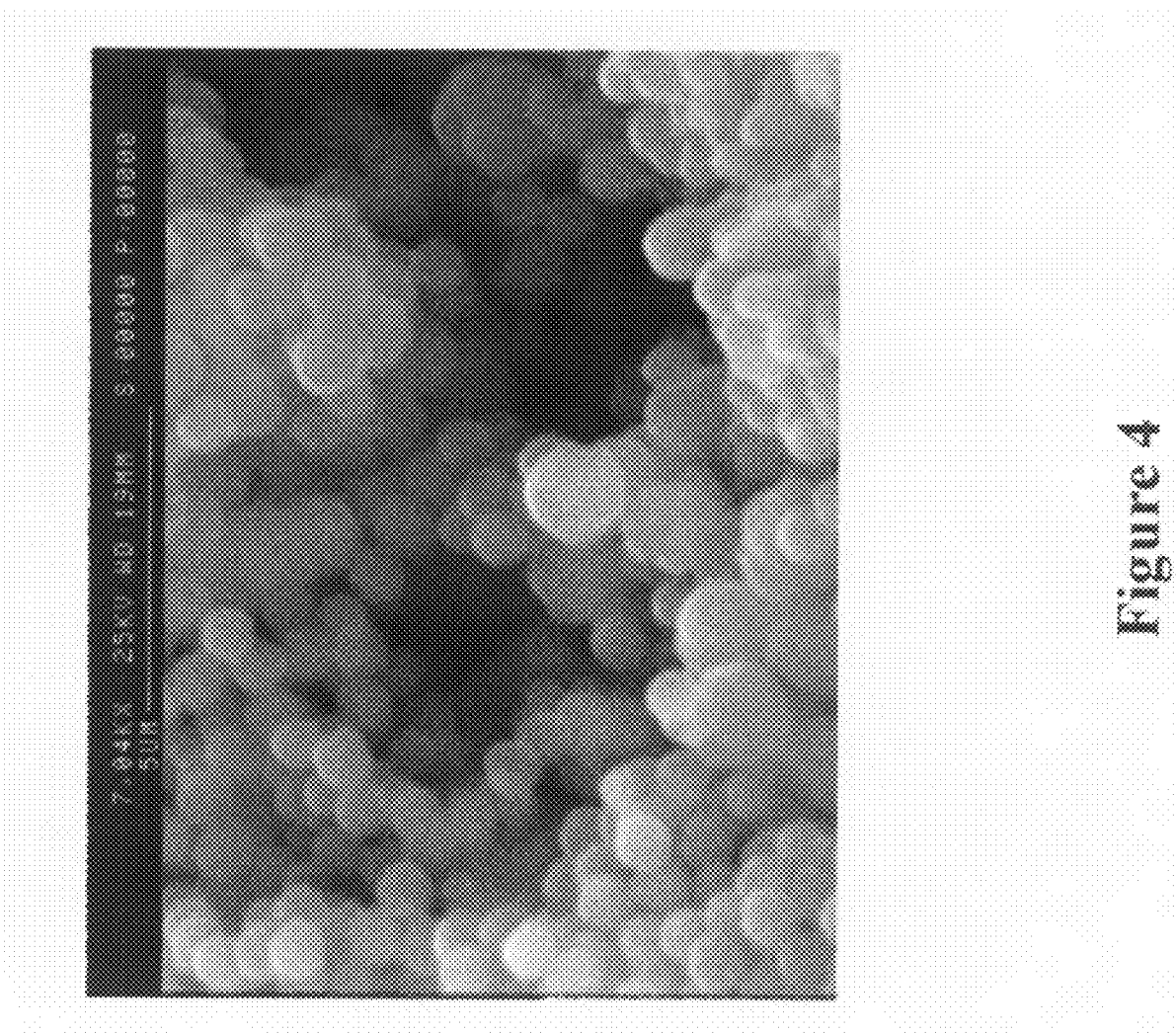
FIG. 4 is a scanning electron microscopy (SEM) image of QD-containing dispersion beads produced using the large-scale dispersion polymerisation procedure set out below.
Figure 5:
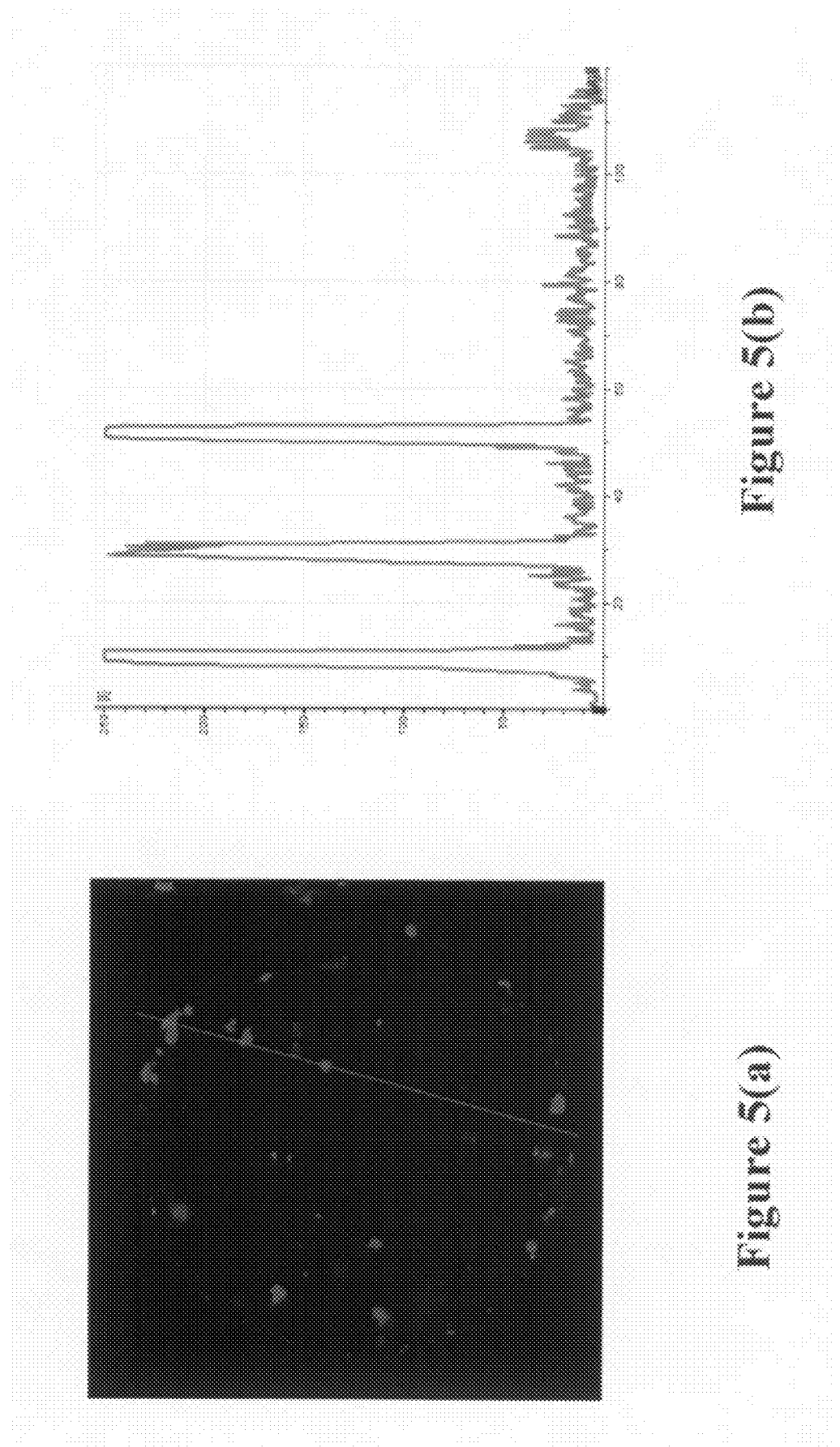
FIG. 5($a$) a confocal microscope image of a suspension bead encapsulated within a thin film of PDMS.
Figure 6:
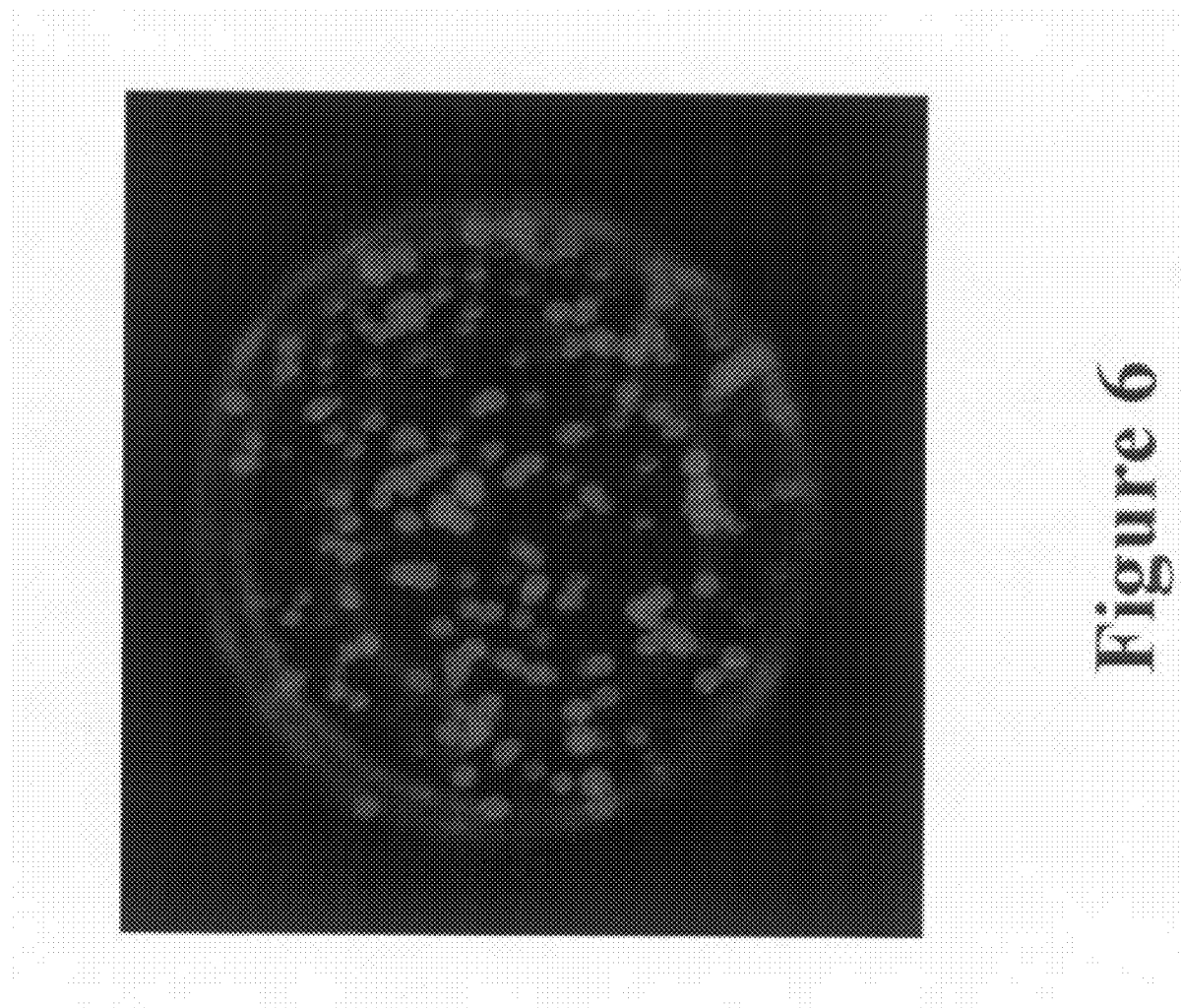
FIG. 6 is a vertical view down a PDMS-based rod that encapsulates QD-containing beads generated using a small scale suspension polymerisation reaction as set out below.
Figure 7:
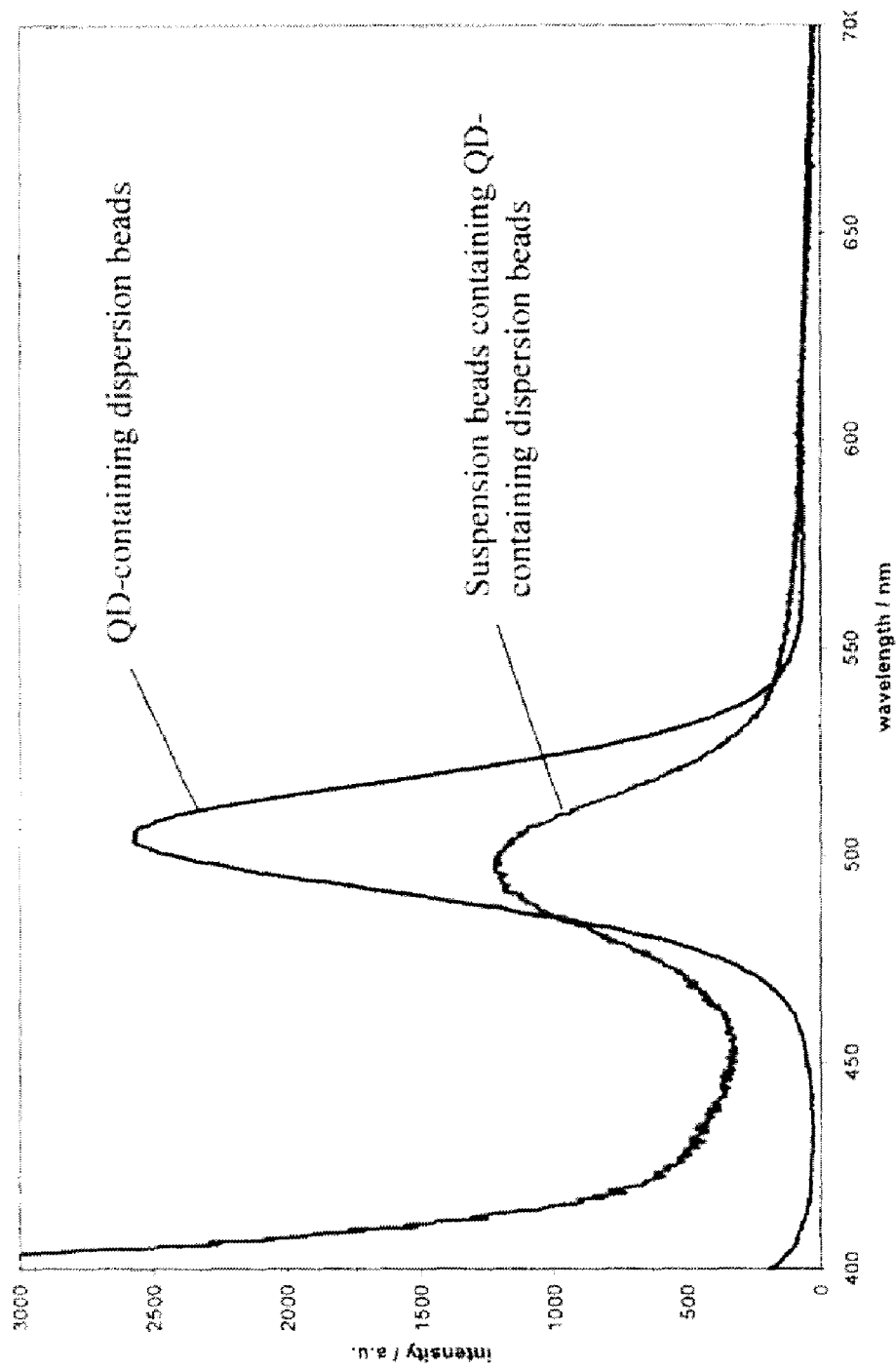
FIG. 7 shows superimposed PL spectra of a sample of QD-containing dispersion beads and a sample of suspension beads that contain the QD-containing dispersion beads.
Figure 8:
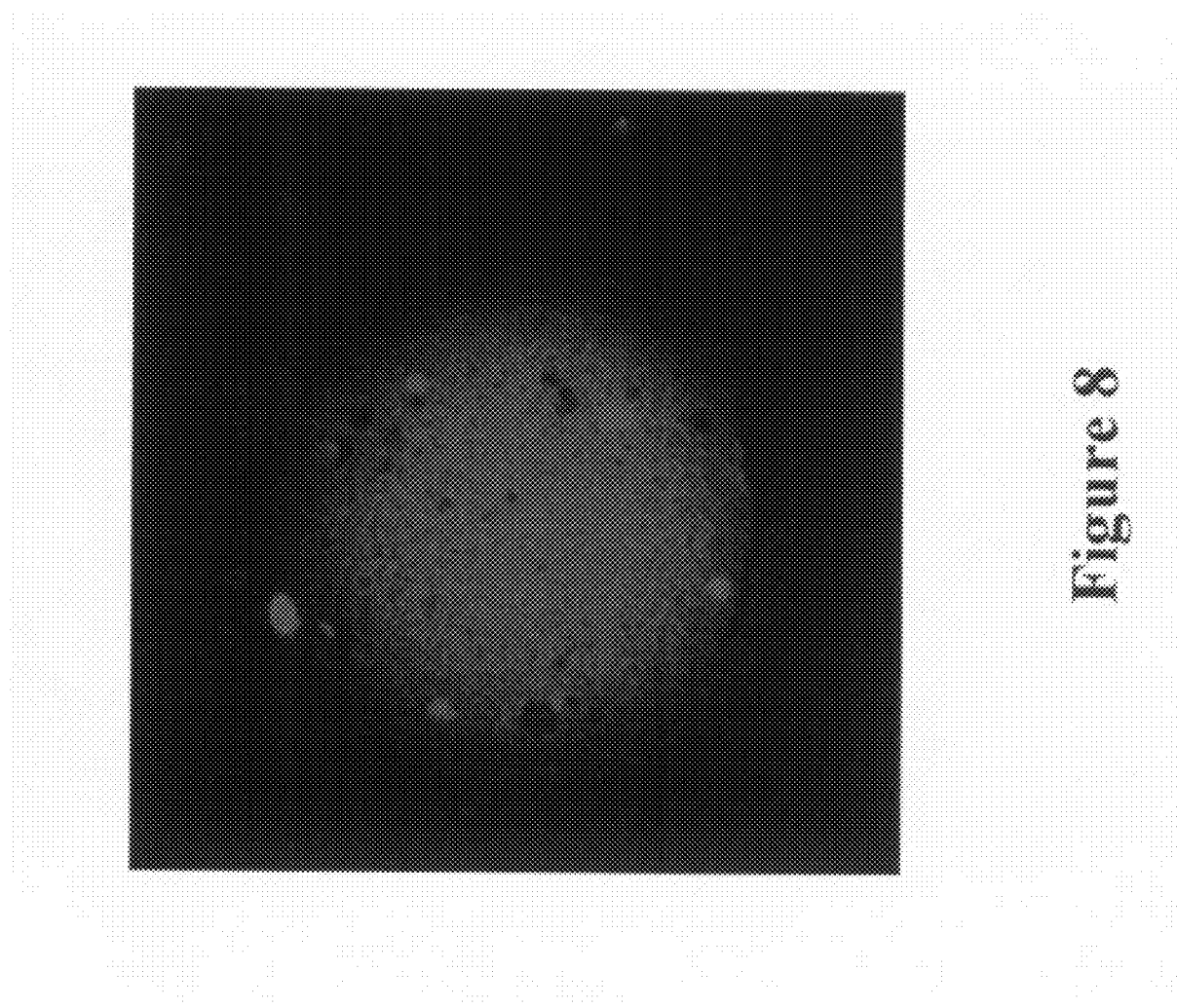
FIG. 8 is a confocal microscopy image of a bead from within a sample of suspension beads that contain the QD-containing dispersion beads (made according to entry 7 of Table 2 below).

Reference is now made to FIG. 3 which compares intensity based sorts of the prior art labelled beads and those of the invention. Graphs (A) and (B) of FIG. 3 are effectively the same plots as represented by the upper graph of FIG. 2. Graph (C) of FIG. 3 is effectively the same plot as represented by the lower graph of FIG. 2.

Assume that it is desired to sort the prior art beads into different fractions. Graph (A) represents an intensity based sort carried out at two different intensities. In principle, this gives three populations of beads a, b and c. However beads having intensities close to the "sorting intensities" may be mis-sorted if the procedure is carried out again, for example after subjecting the beads to a biological assay procedure, and the difference in emission intensity between individual beads is very small.

For the purposes of Graph (B) it is assumed that the prior art particles have initially been sorted at Intensities $I_1$ and $I_2$ into three fractions a, b and c (as represented by Graph (A)). Each fraction is now subjected to a secondary sort. More specifically, fraction a is subjected to a sort at intensity $I_3$ ($<I_1$). This sort separates fraction a into two sub-fractions $a_1$ and $a_2$. The latter fraction is then discarded.

Fraction c is subjected to a secondary sort at an intensity $I_4$ ($>I_2$) so that two sub-fractions $c_1$ and $c_2$ are generated (having intensities below and above $I_4$ respectively). Fraction $c_1$ is discarded.

Consider now the situation represented by Graph C for particles in accordance with the invention. Four primary sorts at different intensities give five distinctly different bead populations readily discriminated from one another on the basis of their quantum dot emission intensities. This procedure is highly efficient both in terms of the number of sorting procedures required and in the fact that no material need be discarded.

The invention is illustrated by the following non-limiting Examples.

EXAMPLES

1. Materials

Cadmium oxide, oleic acid, octadecene, divinylbenzene, styrene, sulfur, poly (N-vinylpyrrolidone) (PVP, molecular mass: 40,000), poly (vinyl alcohol) (PVA, molecular mass: 85,000), and 1,1'-azobis-(cyclohexanecarbonitrile) (ACHN)

were purchased from Aldrich, Fisher and Lancaster and were used without any further purification. Methanol, toluene, acetone and chloroform were purchased from VWR and used as received. Deuterated chloroform was purchased from Goss Scientific and used as received.

All syntheses and manipulations were carried out under a dry oxygen-free argon or nitrogen atmosphere using standard Schlenk and glove box techniques. All solvents were analytical grade and distilled from appropriate drying agents prior to use (Na/K-benzophenone for THF, $Et_2O$, toluene, hexanes, pentane; magnesium for methanol and ethanol and calcium hydride for acetone).

2. Synthesis of CdSe/ZnS and CdSe Nanoparticles

CdSe nanoparticles were synthesized the method disclosed in WO-A-05106082.

Preparation of CdSe-HDA Capped Nanoparticles

Hexadecylamine HDA (500 g) was placed in a three-neck round bottomed flask and dried and degassed by heating to 120° C. under a dynamic vacuum for >1 hour. The solution was then cooled to 60° C. To this was added 0.718 g of $[HNEt_3]_4[Cd_{10}Se_4(SPh)_{16}]$ (0.20 mmols). In total 42 mmols, 22.0 ml of TOPSe and 42 mmols, (19.5 ml, 2.15 M) of $Me_2Cd.TOP$ was used. Initially 4 mmol of TOPSe and 4 mmols of $Me_2Cd.TOP$ were added to the reaction at room temperature and the temperature increased to 110° C. and allowed to stir for 2 hours. The reaction was a deep yellow colour, the temperature was progressively increased at a rate of ~1° C./5 min with equimolar amounts of TOPSe and $Me_2Cd.TOP$ being added dropwise. The reaction was stopped when the PL emission maximum had reached ~600 nm, by cooling to 60° C. followed by addition of 300 ml of dry ethanol or acetone. This produced a precipitation of deep red particles, which were further isolated by filtration. The resulting CdSe particles were recrystallized by re-dissolving in toluene followed by filtering through Celite followed by re-precipitation from warm ethanol to remove any excess HDA, selenium or cadmium present. This produced 10.10 g of HDA capped CdSe nanoparticles. Elemental analysis C=20.88, H=3.58, N=1.29, Cd=46.43%. Max PL=585 nm, FWHM=35 nm. 38.98 mmols, 93% of $Me_2Cd$ consumed in forming the quantum dots.

3. Preparation of CdSe/ZnS-HDA Capped Nanoparticles

HDA (800 g) was placed in a three neck round-bottom flask, dried and degassed by heating to 120° C. under a dynamic vacuum for >1 hour. The solution was then cooled to 60° C., to this was added 9.23 g of CdSe nanoparticles that have a PL maximum emission of 585 nm. The HDA was then heated to 220° C. To this was added by alternate dropwise addition a total of 20 ml of 0.5M $Me_2Zn.TOP$ and 0.5M, 20 ml of sulfur dissolved in octylamine. Three alternate additions of 3.5, 5.5 and 11.0 ml of each were made, whereby initially 3.5 ml of sulphur was added dropwise until the intensity of the PL maximum was near zero. Then 3.5 ml of $Me_2Zn.TOP$ was added dropwise until the intensity of the PL maximum had reached a maximum. This cycle was repeated with the PL maximum reaching a higher intensity with each cycle. On the last cycle, additional precursor was added once the PL maximum intensity been reached until it was between 5-10% below the maximum intensity, and the reaction was allowed to anneal at 150° C. for 1 hour. The reaction mixture was then allowed to cool to 60 ° C. whereupon 300 ml of dry "warm" ethanol was added which resulted in the precipitation of particles. The resulting CdSe—ZnS particles were dried before re-dissolving in toluene and filtering through Celite followed by re-precipitation from warm ethanol to remove any excess HDA. This produced 12.08 g of HDA capped CdSe—ZnS core-shell nanoparticles. Elemental analysis C=20.27, H=3.37, N=1.25, Cd=40.11, Zn=4.43%; Max PL 590 nm, FWHM 36 nm.

4. Ligand Exchange

Quantum dots were dissolved in 1,4-dioxane, 4 ml, containing a large excess of the polymerisable ligand, 1 mmol. The solution was then stirred for 20 hours at room temperature. Centrifugation and drying resulted in ligand exchanged quantum dots (14 mg for the p-vinylbenzylDOPO and 10 mg for p-octenylDOPO batches). Product structures were confirmed by $^1H$ and $^{13}C$ NMR and APCI mass spectrometry.

5. Small-scale Suspension Polymerisation Procedure 1

Aqueous polvinylalcohol (PVA) solution (20 ml, 1% wt/wt, 87-89% hydrolyzed PVA, average MW 85,000-146,000) was prepared and transferred to the reaction vessel (screw cap boiling tube attached to a $N_2$/vacuum manifold system) and degassed with $N_2$ for 20 minutes. A monomer mixture—styrene (10 mmol), divinylbenzene and quantum dots—was prepared and stirred for 5 minutes. AIBN (76 µmol) was added to the monomer mixture then the resultant mixture was stirred for a further 15 minutes with $N_2$ degassing. The dark orange monomer solution (colour due to the quantum dots) was added to the PVA solution while rapidly stirring with a cross-shaped magnetic stirrer. A two phase system resulted with orange droplets being suspended in the colourless aqueous PVA solution. The suspension was stirred at room temperature for 30 minutes before the temperature was increased to 70° C. and stirring was continued for a further 4 hours. The resin beads were then collected over a 38 µm sieve and washed in situ with copious amounts of water. The damp beads were then transferred to a sintered funnel and washed with methanol (100 $cm^3$), MeOH/THF, 1/1 (100 $cm^3$), THF (100 $cm^3$), $CH_2Cl_2$ (100 $cm^3$) and acetone (100 $cm^3$).

6. Small-scale Dispersion Polymerisation Procedure 2

A reaction medium comprising poly(N-vinylpyrrolidone), average MW 55000, (0.2 g) dissolved in a 95:5 ethanol:water mixture (10 ml) was placed in a reaction tube of a 12-place stirring carousel. To this reaction medium was added a monomer mixture comprised of 10 mmol of monomer/crosslinker in total. By way of example (entry 5 below) the monomer comprised of styrene (2 mmol), divinylbenzene (8 mmol) AIBN (0.01 g) and quantum dots (5 mg). Nitrogen was then bubbled though the resultant mixture for 20 minutes and the solution kept under a nitrogen atmosphere until the reaction had proceeded to completion. The solution was gently stirred (approximately 150 rpm) and brought to and maintained at a temperature of 60° C. for 16 hours. The beads were then collected and washed by centrifugation

TABLE 1

| Entry | Monomers | Quantum Dot | Reaction Scale | PL λmax; intensity |
| --- | --- | --- | --- | --- |
| 1 | S/DVB 100/0 | 5 mg CdSe/ZnS; 590 nm | 10 ml | 570; 2200 |
| 2 | S/DVB (98/2) | 5 mg CdSe/ZnS; 590 nm | 10 ml | 564; 3400 |
| 3 | S/DVB (98/2) | 5 mg QDQW ZnS/CdSe/ZnS; 494 nm | 10 ml | 506; 2570 |
| 4 | S/DVB (0:100) | 5 mg QDQW ZnS/CdSe/ZnS; 494 nm | 10 ml | 506; 3334 |
| 5 | S/DVB (20:80) | 5 mg QDQW ZnS/CdSe/ZnS; 494 nm | 10 ml | 506; 3906 |
| 6 | S/DVB (40:60) | 5 mg QDQW ZnS/CdSe/ZnS; 494 nm | 10 ml | 504; 2147 |

Representative examples of quantum dot-containing beads made according to the above "Small-scale dispersion polymerisation procedure 2" and associated PL data. (S—styrene; DVB—divinylbenzene and DOPO—dioctylphosphine oxide)

7. Large-scale Dispersion Polymerisation Procedure.

Styrene (481 mmoles, 55 cm$^3$), divinylbenzene (9.0 mmoles, 1.37 ml), AIBN (3.0 mmoles, 0.5 g) and CdSe/ZnS (hexadecylamine ligand) quantum dots (100 mg) were mixed together. This mixture was then added to a reaction medium comprising poly(N-vinylpyrrolidone), average MW 55000, (10 g) dissolved in a 95:5 ethanol:water mixture (500 ml). Nitrogen was then bubbled though the resultant mixture for 20 minutes and the solution kept under a nitrogen atmosphere until the reaction had proceeded to completion. The solution was gently stirred (approximately 150 rpm) and brought to and maintained at a temperature of 60° C. for 24 hours. The beads were then collected and washed by centrifugation.

8. Procedure for Encapsulating QDs and QD-containing Beads in Polydimethylsiloxane (PDMS)-based Films and Rods.

PDMS (Sylgard 184, Dow Corning) was mixed and prepared as per the manufacturer's instructions, i.e. 10 parts base were mixed with 1 part curing agent and this mixture was then placed under high vacuum until any bubbles had been removed. A small amount of QDs or QD-containing beads (produced by a dispersion or suspension polymerisation reaction) was then added to the PDMS mixture (~1 mg in 1 ml). The resultant mixture was stirred thoroughly and again placed under high vacuum to remove any bubbles.

Thin films were prepared on a microscope slide, by either spreading the PDMS preparation with a spatula or else by placing a drop of the PDMS preparation onto a slide and pressing a cover slip on top. Thin films prepared by either of these two methods were then heated in an oven at 100° C. for 1 hour. Thicker films could similarly be prepared by pouring the liquid PDMS preparation into a suitable mould, e.g. a petri dish, and heating the PDMS preparation in situ at 100° C. Rods were prepared by pouring the PDMS preparation into a glass vial (1 cm diameter×5 cm high) and heating the PDMS preparation in situ at 100° C. for 1 hour.

9. Synthesis of Quantum Dot Doped Polystyrene Beads

CdS doped polystyrene latexes were synthesized via a modification of the suspension polymerization method. PVP (0.25 g) as the stabilizer was first dissolved in 40 ml PVA aqueous solution (wt 10%). The mixture was heated to 50° C. under N$_2$ and a solution of CdS nanoparticles (25 mg), divinylbenzene (20 mg) and ACHN (25 mg) in styrene monomer (2.5 g) was injected into the reaction mixture with vigorous stirring. The reaction was kept at 70° C. for 6 hours. After cooling to room temperature, the solution was purified by centrifugation and redispersion with toluene and water using the method previously described. The size of polymer latexes is strongly dependent on the stirring speed and PVP concentration. With this method, particles with a size range from 100 nm to 500 μm could be obtained.

10. Preparation of the Beads Containing the Quantum Dot-containing Beads.

A small scale suspension polymerisation reaction procedure was carried out exactly as described above with styrene (8 mmol) and divinyl benzene (2 mmol) as the monomer phase (10 mmol in total) and AIBN (76 μmol). The only difference in the procedure employed was that an aliquot of QD-containing dispersion beads (6.5 mg) were added to the monomer mixture, in place of QDs, just prior to the addition of the AIBN.

In addition it was possible to use this method with other ratios of styrene and divinylbenzene and also other monomers in place of styrene and divinylbenzene as the following Table indicates. In all instances the total number of moles in the monomer phase was 10 mmol.

TABLE 2

| Entry | Suspension Monomers | Dispersion Beads (made according to Table 1 entry 3) | PL of the beads containing the quantum dot-containing beads λmax; intensity |
|---|---|---|---|
| 1 | S/DVB 99/1 | 5 mg (494 nm); S/DVB, 99:1 | beads 496; 2592 |
| 2 | S/DVB 98/2 | 5 mg (494 nm); S/DVB, 99:1 | beads 496; 3267 |
| 3 | S/DVB 80/20 | 5 mg (494 nm); S/DVB, 99:1 | beads 487; 892 |
| 4 | S/DVB 60/40 | 5 mg (494 nm); S/DVB, 99:1 | beads 487; 1113 |
| 5 | S/DVB 0/100 | 5 mg (494 nm); S/DVB, 99:1 | beads 487; 3313 |
| 6 | MMA/EGDM 99/1 | 5 mg (494 nm); S/DVB, 99:1 | beads 496; 1391 |
| 7 | MMA/EGDM 98/2 | 5 mg (494 nm); S/DVB, 99:1 | beads 498; 3334 |
| 8 | MMA/EGDM 80/20 | 5 mg (494 nm); S/DVB, 99:1 | beads 498; 2030 |
| 9 | MMA/EGDM 60/40 | 5 mg (494 nm); S/DVB, 99:1 | beads 499; 1130 |
| 10 | MMA/EGDM 0/100 | 5 mg (494 nm); S/DVB, 99:1 | beads 498; 1739 |

Representative examples of beads that contain quantum dot-containing beads made according to the "Preparation of beads containing the quantum dot-containing beads" procedure and associated PL data. (S—styrene; DVB—divinylbenzene; MMA—methyl methacrylate; EGDM—ethylene glycol dimethacrylate).

What is claimed is:

1. A labeled polymeric bead wherein individual beads comprise:
   (a) a primary particle formed of a synthetic polymeric material, and
   (b) at least one secondary particle entrapped within the primary particle of the bead and being comprised of a synthetic polymer material incorporating at least around 500 reporter moieties,
   wherein the reporter moieties are quantum dots.

2. A bead as claimed in claim 1 wherein the primary particle has a maximum cross-sectional dimension of 500 μm.

3. A bead as claimed in claim 2 wherein the primary particle has a maximum cross-sectional dimension of 5 to 200 μm.

4. A bead as claimed in claim 2 wherein the at least one secondary particle has a maximum cross-sectional dimension of 0.2 to 2 μm.

5. A bead as claimed in claim 1 wherein the primary particle includes a plurality of secondary particles.

6. A bead as claimed claim 1 wherein the primary particle contains 1 to 10,000 of the secondary particles.

7. A bead as claimed in claim 6 wherein the primary particle contains 1 to 5000 of the secondary particles.

8. A bead as claimed in claim 7 wherein the primary particle contains 5 to 100 of the secondary particles.

9. A bead as claimed in claim 8 wherein the primary particle contains 20 to 50 of the secondary particles.

10. A labeled polymeric bead wherein individual beads comprise:
(a) a primary particle formed of a synthetic polymeric material, and
(b) at least one secondary particle entrapped within the primary particle of the bead and being comprised of a synthetic polymer material incorporating at least around 500 reporter moieties,
wherein the number of reporter moieties in each secondary particle contained within a primary particle of a bead is at least around 750.

11. A bead as claimed in claim 10 wherein the number of reporter moieties in each secondary particle contained within a primary particle of a bead is at least 1000.

12. A bead as claimed in claim 11 wherein the number of reporter moieties in each secondary particle contained within a primary particle of a bead is at least 10,000.

13. A bead as claimed in claim 12 wherein the number of reporter moieties in each secondary particle contained within a primary particle of a bead is at least 100,000.

14. A bead as claimed in claim 1
wherein the reporter moieties are covalently incorporated in the secondary particles.

15. A collection of polymeric beads wherein individual beads of each polymeric bead comprise:
(a) a primary particle formed of a synthetic polymeric material, and
(b) at least one secondary particle entrapped within the primary particle of the bead and being comprised of a synthetic polymer material incorporating at least around 500 reporter moieties,
wherein individual beads contain the same number of the same type of secondary particles.

16. A collection of polymeric beads wherein individual beads of each polymeric bead comprise:
(a) a primary particle formed of a synthetic polymeric material, and
(b) at least one secondary particle entrapped within the primary particle of the bead and being comprised of a synthetic polymer material incorporating at least around 500 reporter moieties,
wherein the collection of polymeric beads comprises beads containing different combinations of secondary particles.

* * * * *